United States Patent
Hoffmann et al.

(10) Patent No.: US 8,571,173 B2
(45) Date of Patent: Oct. 29, 2013

(54) MAMMOGRAPHY APPARATUS COMPRISING A ROTATABLY MOUNTED FIXTURE FOR AT LEAST TWO X-RAY RECEIVERS

(75) Inventors: Norbert Hoffmann, Nürnberg (DE);
Gerhard Nagengast, Eggolsheim (DE);
Martin Ramsauer, Pyrbaum (DE)

(73) Assignee: Siemens Aktiengesellschaft, München (DE)

( * ) Notice: Subject to any disclaimer, the term of this patent is extended or adjusted under 35 U.S.C. 154(b) by 982 days.

(21) Appl. No.: 12/063,743

(22) PCT Filed: Jul. 20, 2006

(86) PCT No.: PCT/EP2006/064434
§ 371 (c)(1),
(2), (4) Date: May 10, 2010

(87) PCT Pub. No.: WO2007/020150
PCT Pub. Date: Feb. 22, 2007

(65) Prior Publication Data
US 2010/0272231 A1     Oct. 28, 2010

(30) Foreign Application Priority Data
Aug. 18, 2005    (DE) .......................... 10 2005 039 185

(51) Int. Cl.
*H05G 1/02*       (2006.01)
*A61B 6/04*       (2006.01)
*H01J 31/49*      (2006.01)

(52) U.S. Cl.
USPC .............................. 378/37; 378/189; 378/205

(58) Field of Classification Search
USPC .................... 378/37, 98, 98.8, 189, 190, 193, 378/195–197, 204, 205, 208, 210; 128/915; 250/370.01, 370.08, 370.09
See application file for complete search history.

(56) References Cited

U.S. PATENT DOCUMENTS 4,879,736 A *   11/1989   Bergman et al. ............... 378/181
5,170,419 A      12/1992   Johansson et al.
(Continued)

FOREIGN PATENT DOCUMENTS

EP        0 127 073 A1    5/1984
EP        1915093 B1 *   2/2011

OTHER PUBLICATIONS

PCT Search Report/Written Opinion of the International Searching Authority dated Feb. 8, 2008 with English translation.
(Continued)

*Primary Examiner* — Anastadia Midkiff
(74) *Attorney, Agent, or Firm* — Lempia Summerfield Katz LLC

(57) ABSTRACT

A mammography unit having a mounting arm, on which a mounting for at least two X-ray receivers is rotatably disposed in such a way that one X-ray receiver at a time is positioned in an examination position inside an intended X-radiation field, while other X-ray receivers each remain in a reserve position outside the X-radiation field, is provided. The at least one reserve position is disposed on a side located in the X-radiation direction, relative to the mounting arm. In the case of two X-ray receivers, the X-ray receivers each form a lateral angle of between 45° and 90° with the axis of rotation of the mounting. By using a releasable connection of the mounting to the mammography unit, high modularity is provided.

20 Claims, 3 Drawing Sheets

(56) References Cited

U.S. PATENT DOCUMENTS

| | | | |
|---|---|---|---|
| 5,365,562 A | 11/1994 | Toker | |
| 6,242,743 B1 * | 6/2001 | DeVito et al. | 250/363.05 |
| 6,999,554 B2 * | 2/2006 | Mertelmeier | 378/37 |
| 7,127,029 B2 * | 10/2006 | Francke | 378/22 |
| 2005/0226367 A1 * | 10/2005 | Francke | 378/22 |
| 2006/0098777 A1 * | 5/2006 | Hoheisel | 378/98.8 |

OTHER PUBLICATIONS

PCT International Search Report and Written Opinion dated Jan. 12, 2007.

* cited by examiner though the X-ray receivers can be interchanged in modular fashion, it is unnecessary for a worker to change the X-ray receivers manually. Instead, the X-ray receivers can be changed by rotating the mounting.

MAMMOGRAPHY APPARATUS COMPRISING A ROTATABLY MOUNTED FIXTURE FOR AT LEAST TWO X-RAY RECEIVERS

The present patent document is a §371 nationalization of PCT Application Serial Number PCT/EP2006/064434, filed on Jul. 20, 2006, designating the United States, which is hereby incorporated by reference. This patent document also claims the benefit of DE 10 2005 039 185.0, filed Aug. 18, 2005, which is also hereby incorporated by reference.

BACKGROUND

The present embodiments relate to a mammography unit.

A mammography unit is an X-ray system for examining a breast of a male or female patient. Typically, various X-ray receivers are available for the radiological examination, and changes may be made among the X-ray receivers to suit the particular examination. Each of the X-ray receivers is an object table, on which the breast is placed. Both analog X-ray receivers (e.g., X-ray film cassettes) and digital X-ray receivers (e.g., digital X-ray detectors) are known. The X-ray receivers can be interchanged in modular fashion, for example, using a detachable connection of the X-ray receivers with a mounting of the mammography unit.

From U.S. Pat. No. 5,170,419, a mammography unit is known that has a mounting arm, on which a mounting for at least two X-ray receivers is rotatably disposed. The rotatable disposition is configured such that one X-ray receiver at a time, in the form of an X-ray film cassette, can be positioned in an examination position inside an intended X-radiation field with which an X-ray image is made during the examination, while the other X-ray receivers each remain in a respective reserve position outside the X-radiation field. This makes a fast change of format for the applicable X-ray receiver possible.

In the aforementioned mammography unit, the mounting for the X-ray receivers must surround the mounting arm annularly; this structural design is complicated and makes maintenance more difficult.

SUMMARY AND DESCRIPTION

The present embodiments may obviate one or more of the drawbacks or limitations in the related art. For example, in one embodiment, the construction of a mammography unit with a rotatable mounting for at least two X-ray receivers may be improved.

By the disposition of at least one reserve position on a side located in an X-radiation direction relative to a mounting arm, it is possible to connect a mounting for X-ray receivers to a mammography unit in a structurally simple way. It is unnecessary for the mounting arm to be annularly surrounded by the mounting as in U.S. Pat. No. 5,170,419, and thus, the mounting may be changed in modular fashion on the mammography unit. Because the reserve position is disposed on the side of the mounting arm that is located in the X-radiation direction relative to the mounting arm, the freedom in positioning an X-ray emitter for generating an X-radiation field is not restricted by the reserve position, and hence, a more-compact equipment structure is made possible. In this way, despite a rotatable mounting for at least two X-ray receivers, a stable equipment structure is possible in an uncomplicated way.

In a mammography unit, the X-ray emitters, the position of a breast to be examined, and the X-ray receiver intended for the examination are located in a linear disposition to one another. In the examination, the X-radiation is emitted by the X-ray emitter in the direction of the X-ray receiver, and the X-radiation field penetrates the breast to be examined. The X-radiation field may be this direction in which the X-radiation is emitted.

Using a releasable connection (e.g., a connection mechanism) of the mounting to the mammography unit, high modularity is attained. As a result, the mounting may be retrofitted and replaced in a simple way. For example, a mammography unit that, as shipped, is of the analog type may be retrofitted later to a digital mammography unit by replacing the mounting. The mammography unit may also be shipped initially with a rigid mounting for one X-ray receiver, and the rigid mounting may be replaced with the rotatable mounting at a later time. In one embodiment, the connection mechanism may be, for example, a clamp connection or plug-in connection.

Releasably connecting the X-ray receivers to the mounting makes it possible, with a single mounting, to furnish a different assortment of X-ray receivers. In addition, easy replacement of the X-ray receivers for maintenance is made possible.

Because the X-ray receivers held by the mounting each have the same lateral angle to an axis of rotation of the mounting, it is assured in a simple manner that by rotating the mounting, all the X-ray receivers may be disposed at the same examination position. In the case of X-ray receivers that each have a plane receiver surface, the receiver surfaces are at a tangent to a jacket face of an imaginary rectilinear cone of circular cross section, which has an axis of symmetry that coincides with the axis of rotation of the mounting. The lateral angle corresponds to the opening angle of the circular cone. Each X-ray receiver is disposed essentially at the same distance from the mounting when one X-ray receiver is in the examination position.

A lateral angle of approximately 90° is structurally simple to achieve; with such a lateral angle, the X-ray receivers are all located essentially in the same plane.

In one embodiment, a compact, space-saving equipment structure is made possible by using a lateral angle of approximately 45°. If there are only two X-ray receivers, which are disposed on opposite sides relative to the mounting, the two X-ray receivers, at a lateral angle of approximately 45°, form an angle of approximately 90°.

In one embodiment, good utilization of space is made possible by using an approximately equal radial angle difference of adjacent X-ray receivers relative to the rotation about the axis of rotation of the mounting. The X-ray receivers in respective reserve positions minimally restrict the freedom of motion of workers and the patient. In one embodiment, where there are only two X-ray receivers, the radial angle difference is 180° each, so that the two X-ray receivers are disposed on diametrically opposed sides of the mounting.

In one embodiment, good accessibility to the patient is made possible, by using a disposition of the at least one reserve position on a side remote from the patient, relative to the examination position. This disposition may be attained, for example, by securing the mounting to the mounting arm at a point remote from the patient.

In a structurally simple way, the mounting arm is disposed on a substantially vertically aligned tripod, about the at least one reserve position on the side near the tripod relative to the examination position. Because the at least one reserve position is disposed near the tripod, a compact equipment structure and a center of gravity that is close to the tripod are provided. In one embodiment, the mounting arm is adjustable in height on the tripod.

In a structurally simple way, the X-ray emitter is disposed on the mounting arm. In the case of an adjustable-height mounting arm, both the X-ray emitter and the X-ray receivers are adjustable in height jointly with the mounting arm in a simple way. In one embodiment, the arrangement including the mounting arm, the X-ray emitter and the X-ray receiver in the examination position is in the form of a U-shaped arm.

In one embodiment of the mounting arm, the mounting arm is rotatable about a substantially horizontal axis, such that the breast to be examined may be examined from various viewing angles. A mounting arm that is rotatable about a horizontal axis, with an X-ray emitter and an X-ray receiver, is known from U.S. Pat. No. 5,170,419.

DETAILED DESCRIPTION OF THE DRAWINGS

Figure 1:
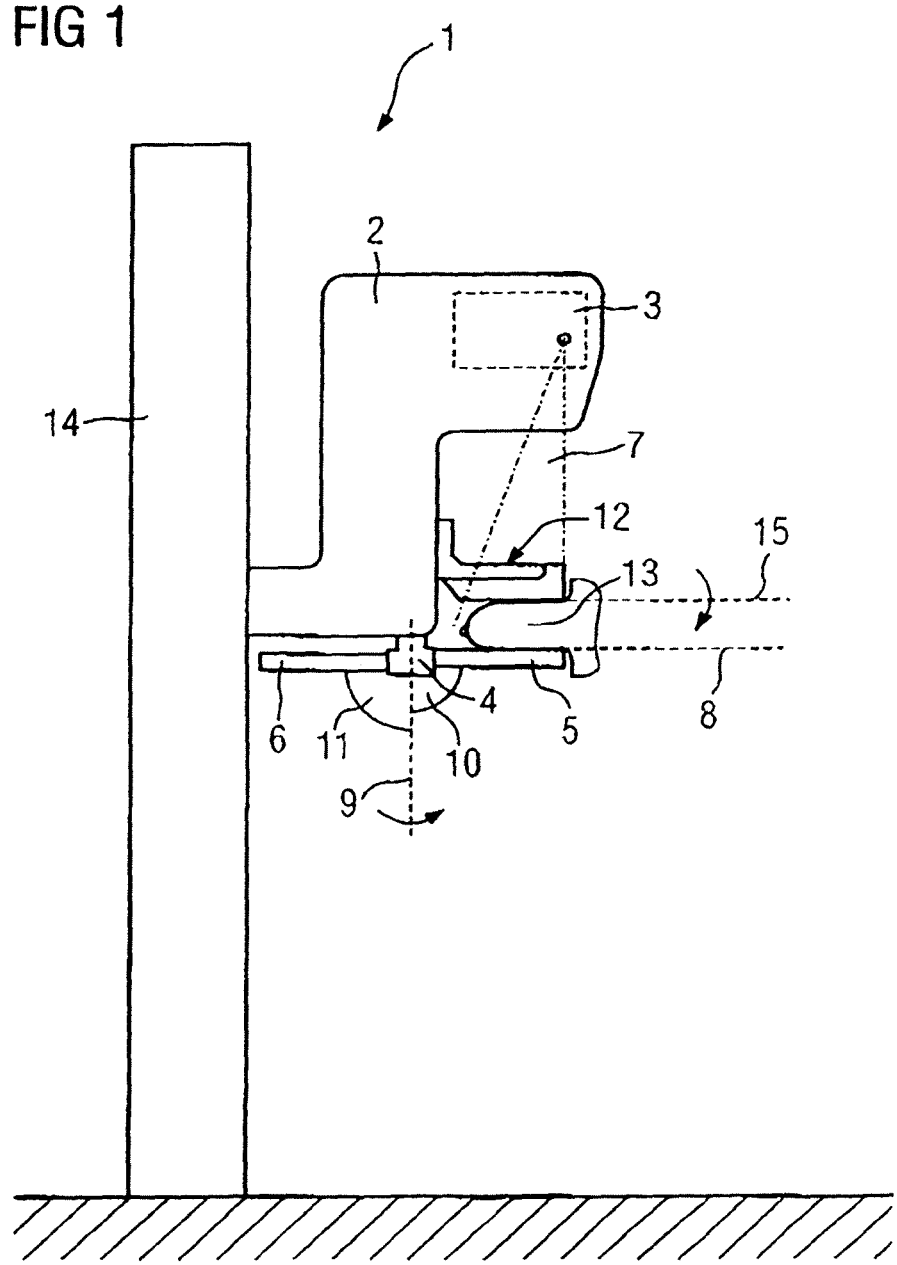
FIG. 1 shows a side view of one embodiment of a mammography unit.

FIG. 1 shows a mammography unit 1 that includes a mounting arm 2, an X-ray emitter 3 disposed on an upper end of the mounting arm 2, and a rotatable mounting 4 disposed on a lower end of the mounting arm 2. In one embodiment, the rotatable mounting 4 is for two X-ray receivers 5, 6 and is disposed such that one X-ray receiver (e.g., X-ray receiver 5) at a time is rotatable in an examination position inside an X-radiation field 7 of the X-ray emitter 3, while another X-ray receiver (e.g., X-ray receiver 6) remains in a reserve position outside the X-radiation field 7. The X-ray receiver 5 in the examination position is aligned with a receiver surface essentially in the direction of the X-ray emitter 3, while the other X-ray receiver 6 is disposed in a reserve position in a plane 8 that is defined by the receiver surface of the one X-ray receiver 5 in the examination position.

The embodiment described above involves a mammography unit 1 for examining a patient in an upright position (e.g., standing or sitting). For adjusting the height to the position of a particular object 13 being examined, the mounting arm 2 is secured to a floor tripod 14 such that the mounting arm 2 may be adjusted in height. For setting various viewing angles in examining the object 13, the mounting arm 2 is pivotable about a horizontal pivot axis 15. For the examination, the particular object 13 being examined is compressed with a compression plate 12 that may be moved down onto the object 13.

The mounting 4, disposed below the mounting arm 2, is releasably connected to the mounting arm 2. In one embodiment, a static mounting for one X-ray receiver may be secured to the mounting arm instead of the rotatable mounting 4. The two X-ray receivers 5, 6 are releasably connected to the mounting 4, and the connections are made via a plug-in mechanism. The plug-in mechanism is locked in the operational state of the mammography unit 1 and may be mechanically unlocked by pressing a button in order to replace one of the two X-ray receivers 5, 6.

The mounting 4, together with the X-ray receivers 5, 6, is rotatable about an axis of rotation 9 that is vertical in the basic position of the mounting arm 2, so that the two X-ray receivers 5, 6 may be transposed in positions. In one embodiment, the X-ray receiver 5 and the X-ray receiver 6 form a lateral angle 10 and a lateral angle 11, respectively, of 90° with the axis of rotation 9, so that the two X-ray receivers 5, 6 are disposed in the same plane. The disposition shown in FIG. 1 of the mounting 4 out of sight of the patient behind the compression plate 12 assures that, relative to the examination position, the reserve position is located near the tripod on a side away from the patient. Outer ends of the X-ray receivers 5, 6 each have the same spacing from the axis of rotation 9, so that by rotating, both X-ray receivers 5, 6 may be positioned in the same examination position.

Figure 2:
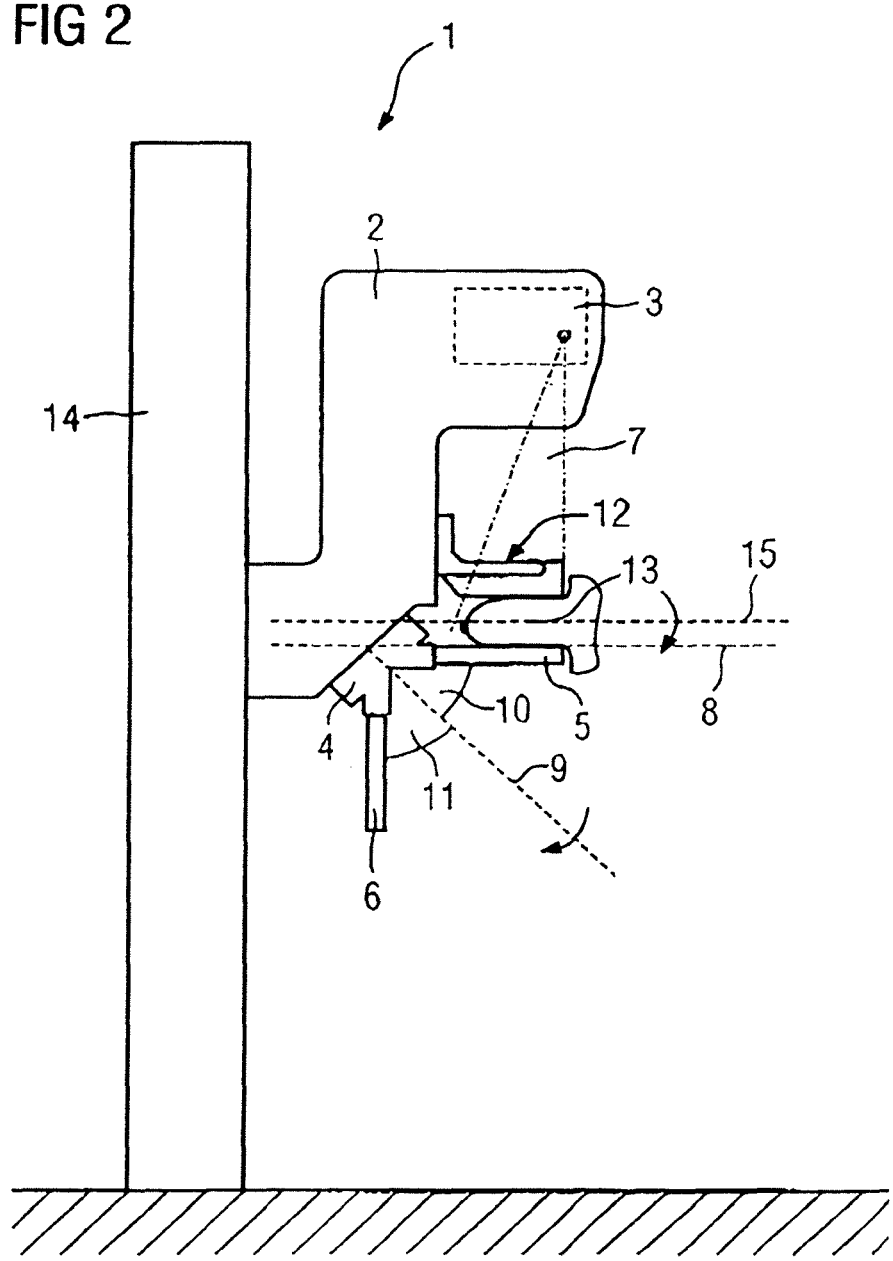
FIG. 2 shows a side view of one embodiment of the mammography unit.

FIG. 2 shows one embodiment of a mammography unit 1, in which the other X-ray receiver 6 is disposed in the reserve position below the plane 8 that is defined by the receiver surface of the one X-ray receiver 5 in the examination position. In this embodiment, the two lateral angles 10, 11 are each 45°, so that together, the two X-ray receivers 5, 6 form a right angle. While the one X-ray receiver 5 in the examination position is aimed at the patient whose breast 13 is being examined with the mammography unit 1, the other X-ray receiver 6 is pointed downward in the reserve position.

As result of this disposition of the mounting 4 and X-ray receivers 5, 6, the center of gravity of the mounting arm 2 with the components secured on it, is shifted closer to the tripod 14, compared to the embodiment shown in FIG. 1. This more-compact construction makes a more-stable equipment structure possible.

Figure 3:
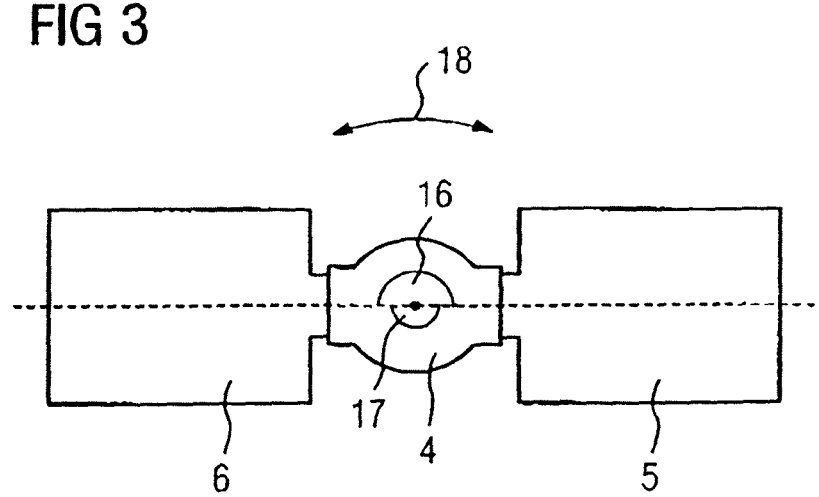
FIG. 3 shows a top view of one embodiment of a mounting for two X-ray receivers.

FIG. 3 shows, in a top view, one embodiment of the mounting 4 of FIG. 1 or FIG. 2 with the two X-ray receivers 5, 6. As in FIGS. 1 and 2, the two X-ray receivers 5, 6 are disposed on diametrically opposed sides of the mounting 4, so that the X-ray receivers 5, 6 each have a radial angle difference 16 and 17, respectively, of 180° in the direction of rotation 18.

Figure 4:
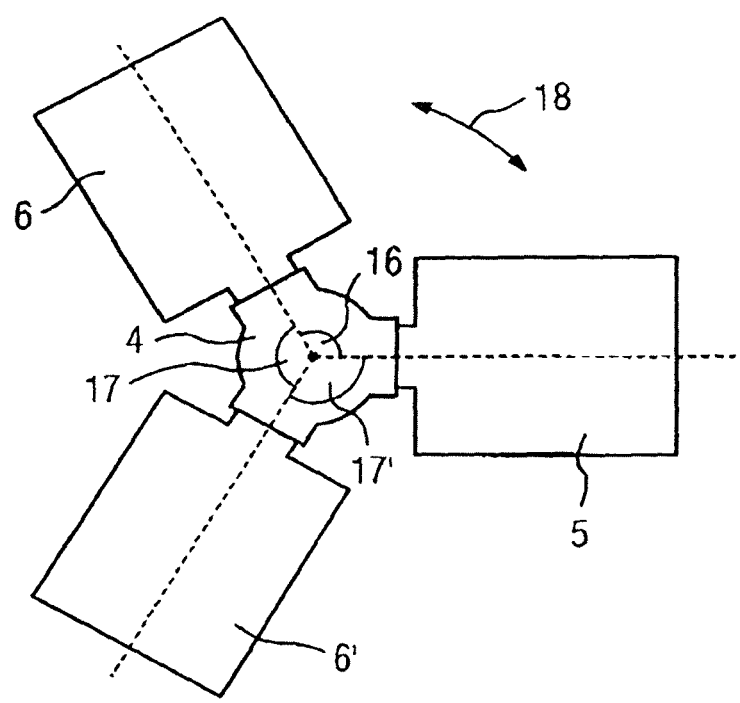
FIG. 4 shows a top view of one embodiment of the mounting for three X-ray receivers.

FIG. 4 shows one embodiment of a mounting 4, as in FIG. 3, with three X-ray receivers 5, 6, 6', each of which forms a respective radial angle difference 16, 17, and 17' with an adjacent X-ray receiver.

The present embodiments may be summarized as follows: The present embodiments relate to a mammography unit having a mounting arm, on which a mounting for at least two X-ray receivers is rotatably disposed such that one X-ray receiver at a time may be positioned in an examination position inside an intended X-radiation field, while other X-ray receivers each remain in a reserve position outside the X-radiation field. The reserve position is disposed on a side located in the X-radiation direction, relative to the mounting arm. If there are two X-ray receivers, the two X-ray receivers each form a lateral angle of between 45° and 90°, for example, with an axis of rotation of the mounting.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:
1. A mammography unit comprising:
a mounting arm;
an X-ray emitter supported by the mounting arm; and
a mounting that holds two X-ray receivers, the mounting being rotatably disposed on the mounting arm, such that one X-ray receiver of the two X-ray receivers is positioned in an examination position within an intended X-radiation field of the X-ray emitter, while the other

X-ray receiver of the two X-ray receivers remains in a reserve position outside the intended X-radiation field of the X-ray emitter, wherein the mounting is rotatable relative to the mounting arm and the X-ray emitter, such that each of the two X-ray receivers is positionable into the examination position within the intended X-radiation field of the X-ray emitter, wherein the reserve position is disposed on a side located in an X-radiation direction relative to the mounting arm, and wherein the mounting is releasably connectable to the mounting arm.

2. The mammography unit as defined by claim 1, wherein the two X-ray receivers are releasably connected to the mounting.

3. The mammography unit as defined by claim 1, wherein the two X-ray receivers held by the mounting each have the same lateral angle with respect to an axis of rotation of the mounting.

4. The mammography unit as defined by claim 3, wherein the lateral angle is approximately 90°.

5. The mammography unit as defined by claim 3, wherein the lateral angle is approximately 45°.

6. The mammography unit as defined by claim 4, wherein a radial angle difference of adjacent X-ray receivers is approximately equal in each case with respect to rotation about the axis of rotation of the mounting.

7. The mammography unit as defined by claim 1, wherein the reserve position is disposed on a side away from the patient, relative to the examination position.

8. The mammography unit as defined by claim 1, further comprising a substantially vertically oriented tripod, on which the mounting arm is disposed,
wherein the reserve position is disposed on a side near the tripod, relative to the examination position.

9. The mammography unit as defined by claim 1, further comprising an X-ray emitter disposed on the mounting arm.

10. The mammography unit as defined by claim 1, wherein the mounting arm is pivotable about a substantially horizontal pivot axis.

11. The mammography unit as defined by claim 2, wherein the two X-ray receivers held by the mounting each have the same lateral angle with respect to an axis of rotation of the mounting.

12. The mammography unit as defined by claim 11, wherein the lateral angle is approximately 90°.

13. The mammography unit as defined by claim 2, wherein the reserve position is disposed on a side away from the patient, relative to the examination position.

14. The mammography unit as defined by claim 2, further comprising a substantially vertically oriented tripod, on which the mounting arm is disposed,
wherein the reserve position is disposed on a side near the tripod, relative to the examination position.

15. The mammography unit as defined by claim 3, further comprising a substantially vertically oriented tripod, on which the mounting arm is disposed,
wherein the reserve position is disposed on a side near the tripod, relative to the examination position.

16. The mammography unit as defined by claim 2, further comprising an X-ray emitter disposed on the mounting arm.

17. The mammography unit as defined by claim 4, further comprising an X-ray emitter disposed on the mounting arm.

18. The mammography unit as defined by claim 8, further comprising an X-ray emitter disposed on the mounting arm.

19. The mammography unit as defined by claim 2, wherein the mounting arm is pivotable about a substantially horizontal pivot axis.

20. The mammography unit as defined by claim 8, wherein the mounting arm is pivotable about a substantially horizontal pivot axis.

* * * * *